US008211544B2

(12) United States Patent
Itami et al.

(10) Patent No.: US 8,211,544 B2
(45) Date of Patent: Jul. 3, 2012

(54) SURFACE MODIFIER

(75) Inventors: Yasuo Itami, Osaka (JP); Tetsuya Masutani, Osaka (JP); Peter C. Hupfield, South Glamorgan (GB); Don Lee Kleyer, Midland, MI (US)

(73) Assignees: Daikin Industries, Ltd., Osaka-shi, Osaka (JP); Dow Corning Corporation, Midland, MI (US)

( * ) Notice: Subject to any disclaimer, the term of this patent is extended or adjusted under 35 U.S.C. 154(b) by 714 days.

(21) Appl. No.: 11/910,356

(22) PCT Filed: Mar. 30, 2006

(86) PCT No.: PCT/JP2006/307261
§ 371 (c)(1),
(2), (4) Date: Feb. 24, 2009

(87) PCT Pub. No.: WO2006/107083
PCT Pub. Date: Oct. 12, 2006

(65) Prior Publication Data
US 2009/0208728 A1 Aug. 20, 2009

Related U.S. Application Data

(60) Provisional application No. 60/667,482, filed on Apr. 1, 2005, provisional application No. 60/740,939, filed on Nov. 30, 2005.

(51) Int. Cl.
*B32B 27/04* (2006.01)
*B32B 17/06* (2006.01)
(52) U.S. Cl. ............ 428/429; 428/447; 528/25; 528/31; 528/42; 528/15
(58) Field of Classification Search .................. None
See application file for complete search history.

(56) References Cited

U.S. PATENT DOCUMENTS

| | | | |
|---|---|---|---|
| 3,189,576 A | 6/1965 | Sweet | |
| 3,646,085 A | 2/1972 | Bartlett | |
| 5,041,588 A | 8/1991 | Caporiccio | |
| 5,202,452 A | 4/1993 | Ogawa et al. | |
| 5,210,253 A | 5/1993 | Kinami et al. | |
| 5,853,800 A | 12/1998 | Dombrowski et al. | |
| 6,296,793 B1 | 10/2001 | Anthes et al. | |
| 7,695,781 B2 * | 4/2010 | Yoneyama et al. | 428/1.32 |
| 2002/0192380 A1 | 12/2002 | Elsbernd et al. | |
| 2005/0224452 A1 | 10/2005 | Spiess et al. | |

FOREIGN PATENT DOCUMENTS

| | | |
|---|---|---|
| EP | 0538061 A2 | 4/1993 |
| EP | 0738771 A1 | 10/1996 |
| EP | 0933377 A2 | 4/1999 |
| JP | 61247743 | 11/1986 |
| JP | 63250389 A | 10/1988 |
| JP | 10120444 | 12/1988 |
| JP | 7016940 | 1/1995 |
| JP | 9-61605 | 3/1997 |
| JP | 09061605 | 3/1997 |
| JP | 09061605 | 7/1997 |
| JP | 9259406 A | 10/1997 |
| JP | 9323997 A | 12/1997 |
| JP | 11029585 A | 2/1999 |
| JP | 2000-94567 | 4/2000 |
| JP | 2000094567 | 4/2000 |
| JP | 2000144097 A | 5/2000 |
| JP | 2001090638 A | 4/2001 |
| JP | 2001-188102 | * 7/2001 |
| JP | 2001-269442 | 10/2001 |
| JP | 2001269942 | 10/2001 |
| JP | 2002056887 T | 3/2002 |
| JP | 2003145971 A | 5/2003 |
| JP | 2003238577 A | 8/2003 |
| JP | 2004146478 A | 5/2004 |
| JP | 2004330664 A | 11/2004 |
| KR | 20030029494 A | 4/2003 |
| WO | 9937720 | 7/1999 |
| WO | 03044075 A1 | 5/2003 |
| WO | 03087935 A2 | 10/2003 |

OTHER PUBLICATIONS

Abstract and machine-generated translation for JP 2001-188102.*
"Sliding Behavior of Water Droplets on Flat Polymer Surface" authorized by Yoshida et al. and published in JACS (2006) 128, 743-747.*
"Dynamic Contact Angle Studies of Self-Assembled Thin Films from Fluorinated Alkyltrichlorosilanes" authorized by Pellerite et al. and published in the Journal of Physical Chemistry, Part B (2002) 106, 47-46-4754.*
Japanese Office Action for Application 2007-544670 issued on Dec. 14, 2010.
Office Action—Corresponding Korean Patent Application No. 10-2007-7025425.
Office Action in European Patent Office, Application No. 06 731 209.0-2115 dated Oct. 27, 2009.
Korean Patent Application No. 10-2007-7025425, Office Action (Final Rejection) issued on Nov. 28, 2009 with English Translation.
Beck et al., "Improving Stamps for 10 NM Level Wafer Scale Nanoimprint Lithography", Microelectronic Engineering, pp. 61-62 (2002) 441-448.
Chen et al., "Effect of Fluoroalkyl Substituents on the Reactions of Alkylchlorosilanes With Mold Surfaces for Nanoimprint Lithography", American Vacuum Society, 3233-3241, Nov. 2004.
Third-Party submission for Japanese Application No. 2007-544670 dated Nov. 24, 2011.
K. Itoh, "Addition Reaction of Silane Having HSi=Linkage to Unsaturated Hydrocarbon", Silicone Handbook, pp. 25-28, Aug. 31, 1990.

* cited by examiner

Primary Examiner — Marc Zimmer
(74) Attorney, Agent, or Firm — Dinsmore & Shohl LLP

(57) ABSTRACT

A surface modifier comprising an organosilicone compound represented by General Formula (A) and/or General Formula (B): $F-(CF_2)_q-(OC_3F_6)_m-(OC_2F_4)_n-(OCF_2)_o(CH_2)_pX(CH_2)_rSi(X')_{3-a}(R^1)_a$ (A) and $F-(CF_2)_q-(OC_3F_6)_m-(OC_2F_4)_n-(OCF_2)_o(CH_2)_pX(CH_2)_r(X')_{2-a}(R^1)_aSiO(F-(CF_2)_q-(OC_3F_6)_m-(OC_2F_4)_n-(OCF_2)_o(CH_2)_pX(CH_2)_r(X')_{1-a}(R^1)_aSiO)_zF-(CF_2)_q-(OC_3F_6)_m-(OC_2F_4)_n-(OCF_2)_o(CH_2)_pX(CH_2)_r(X')_{2-a}(R^1)_aSi$ (B) wherein q is an integer from 1 to 3; m, n, and o are independently integers from 0 to 200; p is 1 or 2; X is O or a bivalent organic group; r is an integer from 2 to 20; $R^1$ is a $C_{1-22}$ linear or branched hydrocarbon group; a is an integer from 0 to 2; X' is hydrolysable group; and z is an integer from 0 to 10 when a is 0 or 1.

21 Claims, No Drawings

SURFACE MODIFIER

CROSS-REFERENCE TO RELATED APPLICATIONS

This application is the National Stage of International Application No. PCT/JP/2006/307,261 filed Mar. 30, 2006, which claims the benefit of U.S. Provisional Application Ser. No. 60/667,482 filed Apr. 1, 2005, and U.S. Provisional Application Ser. No. 60/740,939 filed Nov. 30, 2005.

TECHNICAL FIELD

The present invention is directed to a surface modifier for use in forming a low surface tension layer or a dirt preventive layer on the surface of various substrates, and a method for forming a treated layer using the surface modifier. Moreover, the invention relates to optical members (e.g., antireflective films, optical filters, optical lenses, eyeglass lenses, beam splitters, prisms, mirrors, etc.) wherein the surface modifier is used; antireflective optical members applied to screen surfaces of displays (e.g., liquid crystal displays, CRT displays, projection TVs, plasma displays, EL displays, etc.); optically functional members; display devices in which such an optically functional member is adhered to a display screen surface; treated glasses; treated earthenwares; etc.

RELATED ARTS

Antireflection coatings, optical filters, optical lenses, spectacle lenses, beam splitters, prisms, mirrors and other optical elements and sanitary wares are liable to be stained with fingerprints, skin oil, sweat, cosmetics, etc., when used. Once adhering, such stains are not easily removed, and in particular, stains adhering to optical members with antireflection coatings are easily noticeable and pose problems. Further, windows of automobiles and airplanes are required to have durable water repellency.

To solve such problems relating to stains and water repellency, techniques using various stain-proofing agents have hitherto been proposed.

For example, Japanese Unexamined Patent Publication No. 1997-61605 has proposed a stain-resistant antireflection filter obtained by surface-treating a substrate with a perfluoroalkyl group-containing compound. Japanese Examined Patent Publication No. 1994-29332 has proposed a stain-resistant, low-reflection plastic that has, on its surface, an antireflection coating comprising polyfluoroalkyl group-containing, mono- and disilane compounds and halogen-, alkyl- or alkoxysilane compound. Japanese Unexamined Patent Publication No. 1995-16940 has proposed an optical member obtained by forming a copolymer of perfluoroalkyl (meth)acrylate and alkoxysilane group-containing monomer on an optical thin film mainly consisting of silicon dioxide.

However, the stain-resistant coatings formed by the hitherto known processes have insufficient stain resistance, and in particular, stains such as fingerprints, skin oil, sweat and cosmetics are difficult to be removed therefrom. Further, their stain resistance greatly reduces as they are used for a longer period. Therefore, development of a stain-resistant coating with excellent stain resistance and excellent durability is desired.

SUMMARY OF THE INVENTION

The present invention is to solve the problems of the prior art techniques described above and to provide a surface modifier that can form a superior, low-surface-tension treated layer of high durability that prevents moisture or dirt such as finger prints, skin oil, sweat, cosmetics and the like from adhering to the surface of various substrates, especially antireflective films and like optical members and glasses, and that allows dirt and moisture, once adhered, to be easily wiped off.

Another object of the present invention is to provide a method for producing a surface modifier that can form a superior low surface tension layer.

A further object of the present invention is to provide a method for readily forming a superior low surface tension layer.

Yet another object of the present invention is to provide optical members and various substrates furnished with the superior low surface tension layer.

Yet another object of the present invention is to provide antireflective optical members furnished with the superior low surface tension layer.

Yet another object of the present invention is to provide optically functional members furnished with the antireflective member.

Yet another object of the present invention is to provide display devices having a display screen surface furnished with the optically functional member.

Yet another object of the present invention is to provide the application of the compound of the invention to the field of microfabrication, e.g., nanoimprinting, which has seen significant technical development in recent years, thereby enabling precise mold releasing.

Yet another object of the present invention is to provide the application of the compound of the invention to device production to provide a material and a processing method that allow easy processing of lines having very small width due to the great repellency properties of the compound of the invention.

Yet another object of the present invention is to provide the application of the compound of the invention to the treatment of stoneware such as concrete, limestone, granite or marble.

The present invention provides a dirt preventive agent comprising an organic silicone compound represented by General Formula (A) and/or a partial hydrolysis product, General Formula (B).

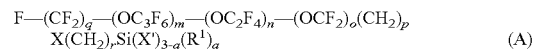

(A)

In General Formula (A), q is an integer from 1 to 3; m, n, and o are independently integers from 0 to 200; p is 1 or 2; X is O or a bivalent organic group; r is an integer from 2-20; $R^1$ is a $C_{1-22}$ linear or branched hydrocarbon group; a is an integer from 0 to 2; and X' is hydrolysable group.

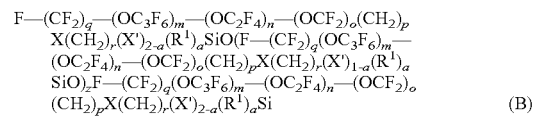

(B)

In General Formula (B), q is an integer from 1 to 3; m, n, and o are independently integers from 0 to 200; p is 1 or 2; X is O or a bivalent organic group; r is an integer from 2-20; $R^1$ is a $C_{1-22}$ linear or branched hydrocarbon group; a is an integer from 0 to 2; X' is hydrolysable group and z is an integer from 0 to 10 with the proviso that a is 0 or 1.

Furthermore, the present invention provides a method for producing the aforementioned surface modifier.

The present invention provides a method for creating a low surface tension using the surface modifier.

The present invention provides a surface of low surface tension obtained by using of the surface modifier.

The present invention provides an optical member furnished with a treated layer containing the surface modifier.

The present invention provides an antireflective optical member furnished with a treated layer containing the surface modifier.

The present invention provides an optically functional member containing the antireflective optical member.

The present invention provides a display device furnished with the optically functional member.

The present invention provides an inorganic substrate, such as glass, having a surface furnished with a treated layer containing the surface modifier.

The present invention provides an automobile and aeronautical glasses and sanitary wares having an inorganic substrate having the aforementioned surface.

The present invention provides an application of the surface modifier to precision mold releasing in nanoimprinting.

The present invention provides a method for readily producing a device having a microstructure using the surface modifier.

MODE OF CARRYING OUT THE INVENTION

Since the surface modifier of the present invention contains a specific organic silicone compound, when a treated layer is created on substrates, e.g., various optical members (antireflective films, optical filters, optical lenses, eyeglass lenses, beam splitters, prisms, mirrors, etc.), using the surface modifier, the adhesion of dirt, such as finger prints, skin oil, sweat, cosmetics and the like, or moisture can be prevented without impairing the optical properties of the optical members, and dirt and moisture, once adhered, can be easily wiped off, thereby giving high durability to the treated layer.

The dirt preventive agent of the present invention contains an organic silicone compound represented by General Formula (A) and/or General Formula (B).

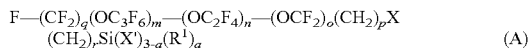

$$F-(CF_2)_q(OC_3F_6)_m-(OC_2F_4)_n-(OCF_2)_o(CH_2)_pX(CH_2)_rSi(X')_{3-a}(R^1)_a \quad (A)$$

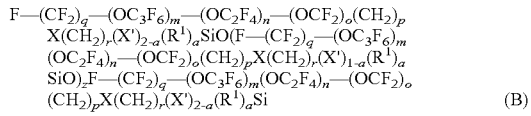

$$F-(CF_2)_q-(OC_3F_6)_m-(OC_2F_4)_n-(OCF_2)_o(CH_2)_p X(CH_2)_r(X')_{2-a}(R^1)_a SiO(F-(CF_2)_q-(OC_3F_6)_m (OC_2F_4)_n-(OCF_2)_o(CH_2)_p X(CH_2)_r(X')_{1-a}(R^1)_a SiO)_z F-(CF_2)_q-(OC_3F_6)_m(OC_2F_4)_n-(OCF_2)_o (CH_2)_p X(CH_2)_r(X')_{2-a}(R^1)_a Si \quad (B)$$

In General Formula (A), q is an integer from 1 to 3; m, n, and o are independently integers from 0 to 200; p is 1 or 2; X is O or a bivalent organic group; r is an integer from 2-20; $R^1$ is a $C_{1-22}$ linear or branched hydrocarbon group; a is an integer from 0 to 2; and X' is hydrolysable group.

In General Formula (B), q is an integer from 1 to 3; m, n, and o are independently integers from 0 to 200; p is 1 or 2; X is O or a bivalent organic group; r is an integer from 2-20; $R^1$ is a $C_{1-22}$ linear or branched hydrocarbon group; a is an integer from 0 to 2; X' is hydrolysable group and z is an integer from 0 to 10 with the proviso that a is 0 or 1.

Preferably, in General Formulas (A) and (B), X is an oxygen atom or a bivalent organic group such as $C_{1-22}$ linear or branched alkylene group;

$R^1$ is a $C_{1-22}$ alkyl group, more preferably a $C_{1-12}$ alkyl group; and X' is chlorine, an alkoxy (—OR) group or —O—N=CR$_2$ wherein R is a $C_{1-22}$ linear or branched hydrocarbon group, particularly a linear or branched alkyl group.

The hydrolysable group, X', of General Formula (A) or (B) are exemplified by groups of the following formulas: alkoxy or alkoxy substituted alkoxy groups such as methoxy, ethoxy, propoxy and methoxyethoxy groups, acyloxy groups such as acetoxy, propionyloxy and benzoyloxy groups, alkenyloxy groups such as isopropenyloxy and isobutenyloxy groups, iminoxy groups such as dimethyl ketoxime, methyl ethyl ketoxime, diethyl ketoxime, cyclohexanoxime groups, substituted amino groups such as methylamino, ethylamino, dimethylamino and diethylamino groups, amido groups such as N-methyl acetamido and N-ethylamido groups, substituted aminoxy groups such as dimethyl aminoxy and diethyl aminoxy groups, halogen, such as chlorine and so on. Among such hydrolysable groups, —OCH$_3$, —OC$_2$H$_5$, and —O—N=C(CH$_3$)$_2$ are particularly preferable. Such hydrolysable groups can be contained in the organic silicone compound of the dirt preventive agent of the present invention as one species or as a combination of two or more species.

In General Formulas (A) and (B), the sum of m, n, and o is preferably 5 or greater, and particularly preferably 10 or greater. X is preferably oxygen and r is preferably 3. In General Formula (A), a is preferably 0.

Among the compounds represented by General Formula (A), a particularly preferable compound, which is represented by General Formula (A) wherein X is oxygen, r is 3, a is 0, and X' is —OCH$_3$, can be synthesized by a hydrosilylation reaction between trichlorosilane and a compound represented by General Formula (C) below in the presence of a transition metal, and then dehydrochlorination by methanol. The use of acid acceptors such as sodium methoxide or trimethyorthoformate are preferred to facilitate the dehydrochlorination.

The catalytic Group VIII transition metals usable in hydrosilylation are preferably Platinum or Rhodium. Most preferred is Platinum. It is preferred to supply Platinum as chloroplatinic acid or as a Platinum complex with 1,3-divinyl-1,1,3,3-tetramethyldisiloxane or Rhodium as tris (triphenylphosphino) Rh$^I$Cl.

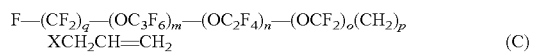

$$F-(CF_2)_q-(OC_3F_6)_m-(OC_2F_4)_n-(OCF_2)_o(CH_2)_p XCH_2CH=CH_2 \quad (C)$$

In General Formula (C), q is an integer from 1 to 3; m, n, and o are independently integers from 0 to 200; p is 1 or 2; X is oxygen or a bivalent organic group.

Specifically, a particularly preferable compound can be produced according to the following reaction scheme.

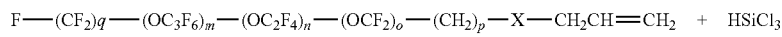

$$F-(CF_2)_q-(OC_3F_6)_m-(OC_2F_4)_n-(OCF_2)_o-(CH_2)_p-X-CH_2CH=CH_2 + HSiCl_3$$

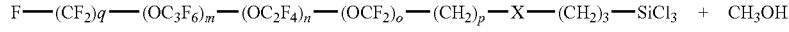

$$F-(CF_2)_q-(OC_3F_6)_m-(OC_2F_4)_n-(OCF_2)_o-(CH_2)_p-X-(CH_2)_3-SiCl_3 + CH_3OH$$

-continued
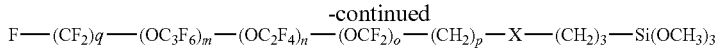

In the reaction scheme above, q is an integer from 1 to 3; m, n, and o are independently integers from 0 to 200; p is 1 or 2; X is oxygen, or a bivalent organic group. Other preferable compounds can be prepared by substituting $HSi(OMe)_3$, or $HSi(OEt)_3$ for $HSiCl_3$ in the above reaction scheme with the added advantage of not requiring dehydrochlorination as a second step.

The hydrosilation reaction is proceeded by reacting for an appropriate time interval and temperature with an excess of silicon hydride to drive the reaction to completion. As an option, an appropriate solvent may be added to facilitate mixing. Various instrumental methods such as Nuclear Magnetic Resonance or Infrared spectroscopy can be used to monitor reaction progress. For example, preferred conditions are 30-90° C. for 1-10 hours with 1.05-30 mol of trichlorosilane per mol of fluorine compound using 0.01-10 mmol of Pt supplied as a Platinum complex with 1,3-divinyl-1,1,3,3-tetramethyldisiloxane catalyst, i.e., a group VIII transition metal. Any excess of silicon hydride can easily be removed from the reaction product by vacuum distillation.

If trichlorosilane was used for the hydrosilation, the second reaction is preferably proceeded by reacting a 0.05-10 molar excess of a mixture of trimethylorthoformate and methanol at 30-70° C. for 1-10 hours per mol of the compound obtained in the first reaction. Various instrumental methods such as Nuclear Magnetic Resonance or Infrared spectroscopy can be used to monitor reaction progress. Any excess of trimethylorthoformate and methanol can easily be removed from the reaction product by vacuum distillation.

Among the fluorine compounds represented by General Formula (C) given above, particularly preferable are those represented by General Formula (C) wherein q is 3, m is 10 to 200, n is 1, o is 0, p is 1, X is oxygen.

Other compounds represented by General Formula (A) can be similarly synthesized according to the reaction scheme above.

Compounds represented by General Formula (B) can be synthesized by a partial hydrolysis and condensation reaction of compounds represented by General Formula (A). Organic silicone compounds represented by General Formula (A) and/or (B) can be used alone or as a combination of two or more species to form the surface modifier of the present invention.

An optional catalyst can be used, if needed, to promote surface modification by the organic silicone compounds represented by General Formula (A) and/or (B). They can be used alone or as a combination of two or more species to form the surface modifier of the present invention. Examples of suitable catalytic compounds include metal salts of organic acids such as dibutyl tin dioctoate, iron stearate, lead octoate and others, titanate esters such as tetraisopropyl titanate, tetrabutyl titanate, chelate compounds such as acetylacetonato titanium and the like. It is preferred to use an amount of the optional catalyst in the range of 0 to 5 parts by weight, for example, 0.001 to 2 parts by weight, and more preferably 0.01 to 2 parts by weight based on 100 parts by weight of the organic silicone compound represented by General Formula (A) and/or (B).

The organic silicone compound of General Formula (A) and/or (B) is an active component of the surface modifier. The surface modifier may consist of the organic silicone compound of General Formula (A) and/or (B). The surface modifier may comprise the organic silicone compound of General Formula (A) and/or (B) and a liquid medium such as an organic solvent. The concentration of the organic silicone compound in the surface modifier is preferably 0.01 to 80% by weight based on the surface modifier.

The organic solvent may be various solvents which preferably dissolve the organic silicone compound provided that the organic solvent does not react with components (particularly, the organic silicone compound) contained in the composition of the present invention. Examples of the organic solvent include a fluorine-containing solvent such as a fluorine-containing alkane, a fluorine-containing haloalkane, a fluorine-containing aromatics and a fluorine-containing ether (for example, hydrofluoroether (HFE)).

The substrate to be treated with the surface modifier of the invention to form a surface-treated layer is not particularly limited. Examples thereof include optical members comprising: inorganic substrates such as glass plates, glass plates comprising an inorganic layer, ceramics, and the like; and organic substrates such as transparent plastic substrates and transparent plastic substrates comprising an inorganic layer; etc.

Examples of inorganic substrates include glass plates. Examples of inorganic compounds for forming glass plates comprising an inorganic layer include metal oxides (silicon oxides (silicon dioxide, silicon monoxide, etc.), aluminum oxide, magnesium oxide, titanium oxide, tin oxide, zirconium oxide, sodium oxide, antimony oxide, indium oxide, bismuth oxide, yttrium oxide, cerium oxide, zinc oxide, ITO (indium tin oxide) and the like; and metal halides (magnesium fluoride, calcium fluoride, sodium fluoride, lanthanum fluoride, cerium fluoride, lithium fluoride, thorium fluoride, etc.).

The inorganic layer or inorganic substrate comprising such an inorganic compound may be single- or multi-layered. The inorganic layer acts as an antireflective layer, and can be formed by known methods such as wet coating, PVD (Physical Vapor Deposition), CVD (Chemical Vapor Deposition), and like methods. Examples of wet coating methods include dip coating, spin coating, flow coating, spray coating, roll coating, gravure coating, and like methods. Examples of PVD methods include vacuum evaporation, reactive deposition, ion beam assisted deposition, sputtering, ion plating, and like methods.

Among usable organic substrates, examples of transparent plastic substrates include substrates comprising various organic polymers. From the viewpoint of transparency, refractive index, dispersibility and like optical properties, and various other properties such as shock resistance, heat resistance and durability, substrates used as optical members usually comprise polyolefins (polyethylene, polypropylene, etc.), polyesters (polyethyleneterephthalate, polyethylenenaphthalate, etc.), polyamides (nylon 6, nylon 66, etc.), polystyrene, polyvinyl chloride, polyimides, polyvinyl alcohol, ethylene vinyl alcohol, acrylics, celluloses (triacetylcellulose, diacetylcellulose, cellophane, etc.), or copolymers of such organic polymers. These substrates can be mentioned as examples of transparent plastic substrates to be treated in the invention.

Examples of usable materials include those prepared by adding known additives such as antistatic agents, UV absorbers, plasticizers, lubricants, coloring agents, antioxidants, flame retardants, etc. to the organic polymers of these organic substrates.

It is also possible to use as the substrate of the invention a substrate prepared by forming an inorganic layer on an organic substrate. In this case, the inorganic layer acts as an antireflective layer and can be formed on an organic substrate by methods as mentioned above.

The inorganic substrate or organic substrate to be treated is not particularly limited. Transparent plastic substrates used as optical members are usually in the form of films or sheets. Such substrates in the form of films or sheets may also be used as the substrate of the invention. A substrate in the form of a film or sheet may be a monolayer or a laminate of a plurality of organic polymers. The thickness is not particularly limited but is preferably 0.01 to 5 mm.

The hard coat layer may be formed between the transparent plastic substrate and the inorganic layer. The hard coat layer improves the hardness of the substrate surface and also flattens and smoothens the surface of the substrate, thus improving the adhesion between the transparent plastic substrate and the inorganic layer. Therefore, scratching caused by pencils or like loads can be prevented. Moreover, the hard coat layer can inhibit cracking in the inorganic layer caused by the bending of the transparent plastic substrate, thus improving the mechanical strength of the optical member.

The material of the hard coat layer is not particularly limited so long as it has transparency, appropriate hardness, and mechanical strength. For example, thermosetting resins and resins cured by ionizing radiation or ultraviolet radiation are usable. UV-curing acrylic resins, organic silicon resins, and thermosetting polysiloxane resins are particularly preferable. The refractive index of such resins is preferably equivalent to or close to that of the transparent plastic substrate.

The coating method for forming such a hard coat layer is not particularly limited. Any method capable of achieving a uniform coating can be used. When the hard coat layer has a thickness of 3 μm or more, sufficient strength can be imparted. A range of 5 to 7 μm is, however, preferable in view of transparency, coating accuracy, and ease of handling.

Furthermore, by mixing and dispersing inorganic or organic particles with a mean particle diameter of 0.01 to 3 μm in the hard coat layer, the optical diffusion treatment generally called "antiglare" can be performed. Although any transparent particles may be used as such particles, low refractive index materials are preferable. Silicon oxides and magnesium fluoride are particularly preferable in terms of stability, heat resistance, etc. Optical diffusion treatment can also be achieved by providing the hard coat layer with an indented surface.

Substrates as mentioned above can be used as the transparent substrate of the antireflective optical member of the invention. In particular, such substrates comprising an antireflective layer on the surface can be transparent substrates comprising an antireflective layer. An antireflective optical member of the invention can be obtained by forming a dirt preventive layer on the surface of such a substrate.

In addition to such optical members, the surface modifier of the invention can be applied to window members for automobiles or airplanes, thus providing advanced functionality. To further improve surface hardness, it is also possible to perform surface modification by a so-called sol-gel process using a combination of the surface modifier of the invention and TEOS (tetraethoxysilane).

By using the surface modifier of the invention as a mold release agent in a nanoimprinting process, precise mold release can be easily achieved. When the surface is treated with the surface modifier of the invention, the modifier diffuses almost to the state of a monolayer, so that the resulting layer has a thickness of only several nanometers. In spite of such a thickness, it is possible to form a surface with a water contact angle of 110° or more and a water drop angle of 5° or less as shown later in the Examples.

The surface modifier of the invention has excellent liquid repellency and thus can be applied to lithography and device formation.

Furthermore, by treating the surface of ceramic materials, it is also possible to produce easily maintained sanitary wares and exterior walls.

The method of forming a treated layer is not particularly limited. For example, wet coating methods and dry coating methods can be used.

Examples of wet coating methods include dip coating, spin coating, flow coating, spray coating, roll coating, gravure coating, and like methods.

Examples of dry coating methods include vacuum evaporation, sputtering, CVD, and like methods. Specific examples of vacuum evaporation methods include resistive heating, electron beam, high-frequency heating, ion beam and like methods. Examples of CVD methods include plasma-CVD, optical CVD, heat CVD, and like methods.

Moreover, coating by atmospheric pressure plasma methods is also possible.

When using wet coating methods, usable diluent solvents are not particularly limited. In view of stability and volatility of the composition, the following compounds are preferable: perfluoroaliphatic hydrocarbons having 5 to 12 carbon atoms, such as perfluorohexane, perfluoromethylcyclohexane, and perfluoro-1,3-dimethylcyclohexane; polyfluorinated aromatic hydrocarbons such as bis(trifluoromethyl)benzene; polyfluorinated aliphatic hydrocarbons, perfluorobutyl methyl ether and like HFEs, etc. Such a solvent can be used singly or as a mixture of two or more.

A wet coating method is preferably used for substrates having complicated shapes and/or large areas.

On the other hand, in consideration of the work environment at the time of forming a dirt preventive layer, dry coating methods, which do not require diluent solvents, are preferable. Vacuum evaporation methods are particularly preferable.

After forming a dirt preventive layer on the substrate by a dry or wet coating method, if necessary, heating, humidification, photoirradiation, electron beam irradiation, etc. may be performed.

The thickness of the dirt preventive layer formed by using the dirt preventive agent of the invention is not particularly limited. A range of 1 to 10 nm is preferable in terms of dirt preventive properties, anti-scratching properties and optical performance of the optical member.

EXAMPLES

The following Examples are intended to illustrate the present invention in detail, and not to limit the scope of the invention.

Synthesis Example 1

To a 1 L 3 neck flask equipped with magnetic stir bar, reflux condenser, temperature control and dry nitrogen headspace purge was added 411.2 g of ($F_3CCF_2CF_2$ ($OCF_2CF_2CF_2$)$_{11}OCF_2CF_2CH_2OCH_2CH\!=\!CH_2$), 286.13 g of 1,3-bis(trifluoromethyl)benzene and 110.47 g of trichlorosilane. The contents were heated to 60° C. before the addition over 3.7 hours of 0.045 g of Pt metal complexed with 1,3-divinyl-1,1,3,3-tetramethyldisiloxane. The contents maintained at 60° C. for an additional 30 minutes to make $F_3CCF_2CF_2(OCF_2CF_2CF_2)_{11}OCF_2CF_2CH_2OCH_2CH_2CH_2SiCl_3$. The residual trichlorosilane and solvent was vacuum stripped from the reaction mixture before addition of 156.5 g of trimethylorthoformate and 1.8 g of methanol. The contents of the flask were maintained at 60° C. overnight to facilitate methoxylation of the chlorosilane. After 14 hours an additional 5.2 g of methanol was added and the temperature maintained for 3 hours. Activated carbon, 2.5 g, was added. Excess reagent was removed under vacuum. The product was filtered through a bed of Celite filter aid on a 5 micron membrane. The product, $F_3CCF_2CF_2(OCF_2CF_2CF_2)_{11}OCF_2CF_2CH_2OCH_2CH_2CH_2Si(OMe)_3$, was isolated as the filtrate. Analysis by infrared and nuclear magnetic resonance spectroscopy showed the complete disappearance of $CH_2=CHCH_2O$ and SiCl functionalities.

Synthesis Example 2

To a 25 mL 2 neck flask equipped with magnetic stir bar, reflux condenser, temperature control and dry nitrogen headspace purge was added 7.52 g of $(F_3CCF_2CF_2(OCF_2CF_2CF_2)_{11}OCF_2CF_2CH_2OCH_2CH=CH_2)$, 12.02 g of 1,3-bis(trifluoromethyl)benzene and 3.91 g of trimethoxysilane. The contents were heated to 100° C. before the slow addition of 1.4E-3 g of Pt metal complexed with 1,3-divinyl-1,1,3,3-tetramethyldisiloxane over 16 hours. After an additional 2 hours, excess reagent was removed under vacuum. The product, $F_3CCF_2CF_2(OCF_2CF_2CF_2)_{11}OCF_2CF_2CH_2OCH_2CH_2CH_2Si(OMe)_3$, was isolated as the flask residue, mixed with activated carbon and filtered. Analysis by infrared and nuclear magnetic resonance spectroscopy showed none of the initial $CH_2=CHCH_2O$ functionality remaining.

Synthesis Examples 2-8

By the same method described in Synthesis Example 1, the following compounds were synthesized.
Synthesized Compound 2;
  $F_3CCF_2CF_2(OCF_2CF_2CF_2)_{21}OCF_2CF_2CH_2OCH_2CH_2CH_2Si(OMe)_3$
Synthesized Compound 3;
  $F_3CCF_2CF_2(OCF_2CF_2CF_2)_{30}OCF_2CF_2CH_2OCH_2CH_2CH_2Si(OMe)_3$
Synthesized Compound 4;
  $F_3CCF_2CF_2(OCF_2CF_2CF_2)_{21}OCF_2CF_2CONHCH_2CH_2CH_2Si(OMe)_3$
Synthesized Compound 5;
  $F_3CCF_2CF_2O[CF(CF_3)CF_2O]_3CF(CF_3)CH_2OCH_2CH_2CH_2Si(OMe)_3$
Synthesized Compound 6;
  $F_3CCF_2CF_2O[CF(CF_3)CF_2O]_3CF(CF_3)CONHCH_2CH_2CH_2Si(OMe)_3$
Synthesized Compound 7;
  $F_3CCF_2CF_2O[CF(CF_3)CF_2O]_4CF(CF_3)CH_2OCH_2CH_2CH_2Si(OMe)_3$
Synthesized Compound 8;
  $F_3CCF_2CF_2O[CF(CF_3)CF_2O]_5CF(CF_3)CH_2OCH_2CH_2CH_2Si(OMe)_3$
Comparative Compound a
Optool DSX (produced by Daikin Industries, Ltd.) was purchased, which is called Comparative Compound a.

Example 1

Pretreatment of Silicon Wafer Substrates

Silicon wafers (2 cm×4 cm×0.7 mm) were ultrasonically treated in acetone at 25° C. for 10 minutes, and washed in sulfuric acid/30 mass % hydrogen peroxide solution=70/30 (V/V) at 100° C. for 1 hour. The wafers were then washed with methanol and ethanol in that order, and dried under reduced pressure at room temperature. Further, UV/ozonization treatment was performed at 70 Pa for 10 minutes, thereby confirming that the water contact angle was 0° C.

Wet Coating with Surface Modifier:

Each of the Synthesized Compounds and Comparative Compound a was diluted with HFE-7200 (manufactured by 3M) to concentrations of 0.05 mass %, 0.10 mass % and 0.50 mass %. The silicon wafers pretreated as above were dipped in the diluted compounds at 25° C. for 30 minutes, and dried at 25° C. for 24 hours. The wafers were then ultrasonically cleaned in HFE-7200 at 25° C. for 10 minutes, and dried under reduced pressure at 25° C. for 1 hour.

Measurement of Contact Angle and Sliding Angle:

The water contact angle and water sliding angle of the treated samples were measured with Model CA-X: Kyowa Interface Science Co., Ltd. The measurement was carried out using droplets of 20 μl of distilled water under the conditions of 20° C. and 65% RH.

Fingerprint Adherence:

The finger was pressed onto the surface of the treated samples to make a fingerprint adhere, and the adherence and noticeability of the fingerprint was visually evaluated according to the following criteria.

A: Fingerprint adhered only slightly and, even if it adhered, was not easily noticeable.

B: Adhesion of fingerprint is noticeable.

Ease of Removing Fingerprint by Wiping:

The fingerprint adhering to the sample surface was wiped with nonwoven cellulose fabric (Bemcot M-3, manufactured by Asahi Chemical Co., Ltd.) to visually evaluate the removability of the fingerprint according to the following criteria.

A: Fingerprint can be completely wiped off.
B: Trace of fingerprint remains after wiping.
C: Fingerprint cannot be wiped off.

Abrasion Resistance:

The sample surface was rubbed 100 times with unwoven cellulose fabric (Bencot M-3, manufactured by Asahi Chemical Co., Ltd.) at a load of 500 gf, and subjected to the above tests.

TABLE 1

|  | Synthesized Compound 1 | | | Comparative Example a | | |
| --- | --- | --- | --- | --- | --- | --- |
|  | 0.05 mass % | 0.10 mass % | 0.50 mass % | 0.05 mass % | 0.10 mass % | 0.50 mass % |
| Contact angle | 115 (114) | 116 (116) | 120 (118) | 114 (112) | 115 (113) | 120 (119) |
| Sliding angle | 3 (3) | 3 (3) | 3 (3) | 40 (45) | 39 (41) | 22 (25) |
| Fingerprint adherence | A (A) | A (A) | A (A) | A (A) | A (A) | A (A) |
| Ease of removing fingerprint | A (A) | A (A) | A (A) | A (B) | A (B) | A (A) |

In Table 1, the parenthesized values are those of the abrasion resistance tests.

Table 1 reveals that the treated layer formed using the surface modifier of the present invention has a water contact angle similar to that of the treated layer of Comparative Example, but has a much smaller water sliding angle, and thus is difficult to wet with water and enables fingerprints to be wiped off easily. The table also shows that these excellent properties are durable.

Example 2

In the same manner as in Example 1, various properties of Synthesized Compounds 2-8 were measured. The results are shown in Tables 2-5.

TABLE 2

|  | Synthesized Compound 2 | | | Synthesized Compound 3 | | |
| --- | --- | --- | --- | --- | --- | --- |
|  | 0.05 mass % | 0.10 mass % | 0.50 mass % | 0.05 mass % | 0.10 mass % | 0.50 mass % |
| Contact angle | 116 (115) | 116 (116) | 120 (118) | 114 (114) | 116 (115) | 120 (119) |
| Sliding angle | 3 (3) | 3 (3) | 3 (3) | 4 (5) | 3 (3) | 3 (3) |
| Fingerprint adherence | A (A) | A (A) | A (A) | A (A) | A (A) | A (A) |
| Ease of removing fingerprint | A (A) | A (A) | A (A) | A (A) | A (A) | A (A) |

TABLE 3

|  | Synthesized Compound 4 | | |
| --- | --- | --- | --- |
|  | 0.05 mass % | 0.10 mass % | 0.50 mass % |
| Contact angle | 115 (113) | 115 (116) | 119 (117) |
| Sliding angle | 4 (4) | 3 (3) | 3 (3) |
| Fingerprint adherence | A (A) | A (A) | A (A) |
| Ease of removing fingerprint | A (A) | A (A) | A (A) |

TABLE 4

|  | Synthesized Compound 5 | | | Synthesized Compound 6 | | |
| --- | --- | --- | --- | --- | --- | --- |
|  | 0.05 mass % | 0.10 mass % | 0.50 mass % | 0.05 mass % | 0.10 mass % | 0.50 mass % |
| Contact angle | 112 (110) | 114 (112) | 115 (113) | 112 (111) | 113 (112) | 114 (113) |
| Sliding angle | 3 (3) | 3 (3) | 2 (3) | 4 (5) | 3 (3) | 3 (3) |
| Fingerprint adherence | A (A) | A (A) | A (A) | A (A) | A (A) | A (A) |
| Ease of removing fingerprint | A (A) | A (A) | A (A) | A (A) | A (A) | A (A) |

TABLE 5

|  | Synthesized Compound 7 | | | Synthesized Compound 8 | | |
| --- | --- | --- | --- | --- | --- | --- |
|  | 0.05 mass % | 0.10 mass % | 0.50 mass % | 0.05 mass % | 0.10 mass % | 0.50 mass % |
| Contact angle | 113 (112) | 115 (114) | 116 (115) | 114 (113) | 114 (113) | 116 (115) |
| Sliding angle | 3 (4) | 3 (3) | 2 (3) | 3 (4) | 3 (3) | 2 (3) |
| Fingerprint adherence | A (A) | A (A) | A (A) | A (A) | A (A) | A (A) |
| Ease of removing fingerprint | A (A) | A (A) | A (A) | A (A) | A (A) | A (A) |

Table 2, Table 3, Table 4 and Table 5 show the same results as described in Table 1.

Effects of the Invention

The treated layer formed on a substrate surface using the surface modifier of the present invention has a much smaller sliding angle than the treated layer formed using a hitherto known treatment agent, and thus is more resistant to stains such as fingerprints, skin oil, sweat and cosmetics. Further, even if such stains adhere to the treated layer of the surface modifier of the invention, they are readily wiped off. Furthermore, such properties are stably exhibited.

Moreover, the optically functional member obtained by bonding the optical element or antireflection optical member of the present invention to an optical functional member, such as a deflection plate, has a treated layer with the above-mentioned excellent functionality and high durability formed on its surface, and therefore provides the display device with high image recognition of the present invention, when bonded to, for example, the front panel of the display screen of various displays (liquid crystal displays, CRT displays, projection displays, plasma displays, EL displays, etc.).

Furthermore, the treated layer formed on a substrate surface using the surface modifier of the present invention is extremely thin and thus has highly precise processability and excellent micromachining properties.

The invention claimed is:

1. A surface modifier comprising an organosilicone compound represented by General Formula (A) and/or General Formula (B):

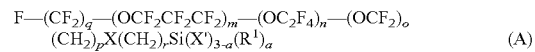

wherein q is an integer from 1 to 3; m, n, and o are independently integers from 0 to 200, provided that the sum of m, n, and o is 5 or greater; p is 1 or 2; X is O; r is 3; $R^1$ is a $C_{1-22}$ linear or branched hydrocarbon group; a is an integer from 0 to 2; and X' is hydrolysable group; and

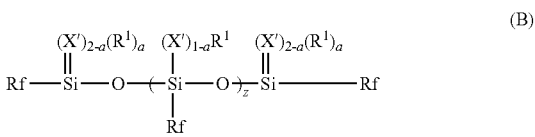

wherein Rf is $F\text{---}(CF_2)_q\text{---}(OC_3F_6)_m\text{---}(OC_2F_4)_n\text{---}(OCF_2)_o(CH_2)_pX(CH_2)_r\text{---}$, wherein q is an integer from 1 to 3; m, n, and o are independently integers from 0 to 200, provided that the sum of m, n, and o is 5 or greater; p is 1 or 2; X is O; r is 3; $R^1$ is a $C_{1-22}$ linear or branched hydrocarbon group; a is an integer from 0 to 2; X' is hydrolysable group; and z is an integer from 0 to 10 when a is 0 or 1.

2. The surface modifier according to claim 1, wherein in General Formula (A) and/or General Formula (B), q is 3, m is an integer from 10 to 200, n is 1, o is 0, p is 1, X is O, r is 3 and a is 0 or 1.

3. The surface modifier according to claim 1, with the addition of a catalyst to promote surface modification.

4. The surface modifier according to claim 1, with the addition of a catalyst to promote surface modification wherein the proportion of compound represented by General Formula (A) and/or General Formula (B) and catalyst is 0.001 to 2 parts by weight based on 100 parts by weight of the organic silicone compound.

5. A method for producing an organosilicone compound represented by General Formula (A):

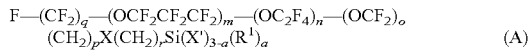

the method using a hydrosilylation reaction between trichlorosilane or trialkoxysilane, and a compound represented by General Formula (C) below in the presence of a transition metal:

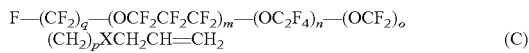

wherein q is an integer from 1 to 3; m, n, and o are independently integers from 0 to 200, provided that the sum of m, n, and o is 5 or greater; p is 1 or 2; $R_1$ is a $C_{1-22}$ linear or branched hydrocarbon group; X is oxygen; and r is 3, X' is chlorine or alkoxy, and a is 0.

6. A method for producing an organosilicone compound represented by General Formula (A):

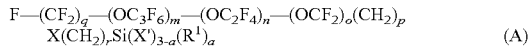

wherein X' is —OR with R being a $C_{1-22}$ linear or branched hydrocarbon group, the method using a hydrosilylation reaction between trichlorosilane and a compound represented by General Formula (C):

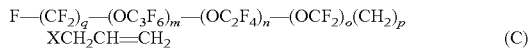

in the presence of a transition metal, and then an alkoxylation reaction in the presence of a neutralizing agent with a $C_{1-22}$ linear or branched aliphatic alcohol, thereby eliminating hydrogen chloride, or an alkoxylation reaction with a metal alkoxide, wherein q is an integer from 1 to 3; m, n, and o are independently integers from 0 to 200; p is 1 or 2; X is O or a bivalent organic group; r is an integer from 2 to 20; $R^1$ is a $C_{1-22}$ linear or branched hydrocarbon group; a is an integer from 0 to 2; and wherein X' is —OR with R being a $C_{1-22}$ linear or branched hydrocarbon group.

7. A method for producing an organosilicone compound represented by General Formula (A):

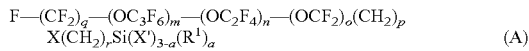

the method using a hydrosilylation reaction between trichlorosilane and a compound represented by General Formula (C):

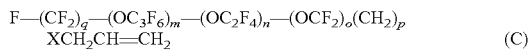

in the presence of a transition metal, and then a reaction with a dialkyl ketoxime represented by HO—N=CR$_2$ with R being a $C_{1-22}$ linear or branched hydrocarbon group, wherein q is an integer from 1 to 3; m, n, and o are independently integers from 0 to 200; p is 1 or 2; X is O or a bivalent organic group; r is an integer from 2 to 20; $R^1$ is a $C_{1-22}$ linear or branched hydrocarbon group; a is an integer from 0 to 2; and wherein X' is —O—N=CR$_2$ with R being a $C_{1-22}$ linear or branched hydrocarbon group.

8. The method for producing an organosilicone compound according to claim 5, wherein the transition metal is platinum or rhodium.

9. A method for producing an organosilicone compound represented by General Formula (B):

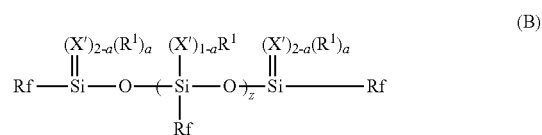

wherein Rf is F—(CF$_2$)$_q$—(OC$_3$F$_6$)$_m$—(OC$_2$F$_4$)$_n$—(OCF$_2$)$_o$(CH$_2$)$_p$X(CH$_2$)$_r$—, wherein q is an integer from 1 to 3; m, n, and o are independently integers from 0 to 200, provided that the sum of m, n, and o is 5 or greater; p is 1 or 2; X is O; r is 3; $R^1$ is a $C_{1-22}$ linear or branched hydrocarbon group; a is an integer from 0 to 2; X' is hydrolysable group; and z is an integer from 0 to 10 when a is 0 or 1; the method comprising partially hydrolyzing and then condensing a compound represented by General Formula (A) that is obtained according to the method recited in claim 5.

10. A treated surface comprising a substrate having a surface modifier thereon, said surface modifier comprising an organosilicone compound represented by General Formula (A) and/or General Formula (B):

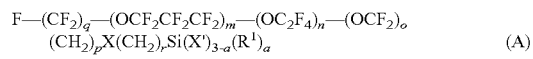

wherein q is an integer from 1 to 3; m, n, and o are independently integers from 0 to 200, provided that the sum of m, n, and o is 5 or greater; p is 1 or 2; X is O; r is 3; $R^1$ is a $C_{1-22}$ linear or branched hydrocarbon group; a is an integer from 0 to 2; and X' is hydrolysable group; and

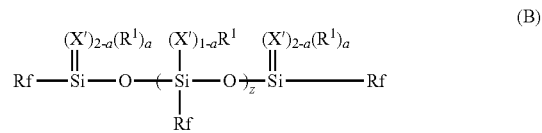

wherein Rf is F—(CF$_2$)$_q$—(OC$_3$F$_6$)$_m$—(OC$_2$F$_4$)$_n$—(OCF$_2$)$_o$(CH$_2$)$_p$X(CH$_2$)$_r$—, wherein q is an integer from 1 to 3; m, n, and o are independently integers from 0 to 200, provided that the sum of m, n, and o is 5 or greater; p is 1 or 2; X is O; r is 3; $R^1$ is a $C_{1-22}$ linear or branched hydrocarbon group; a is an integer from 0 to 2; X' is hydrolysable group; and z is an integer from 0 to 10 when a is 0 or 1; the treated surface having a water contact angle of at least 110° and a water sliding angle of no more than 5°.

11. The treated surface of claim 10 wherein said surface has been formed by forming on a substrate a film of said surface modifier according to a wet coating method.

12. The treated surface of claim 10 wherein said surface has been formed by forming on a substrate a film of the surface modifier according to a dry coating method.

13. The treated surface of claim 10 wherein said surface has been formed by impregnating a porous article with said surface modifier, and forming a treated layer on a substrate by heating in a vacuum the porous article, in which the surface modifier has been impregnated, to evaporate the surface modifier.

14. The treated surface according to claim 13, wherein the porous article comprises at least one species selected from the group consisting of $SiO_2$, $TiO_2$, $ZrO_2$, MgO, $Al_2O_3$, $CaSO_4$, Cu, Fe, Al, stainless steel, and carbon.

15. The treated surface according to claim 13, wherein the surface modifier impregnated in a porous article is evaporated according to at least one heating method selected from resistive heating, electron beam heating, ion beam heating, high-frequency heating, and optical heating.

16. The treated surface according to claim 13 wherein a film is formed on said substrate by nozzle-spraying the surface modifier in the presence of a plasma.

17. The treated surface according to claim 16, wherein the plasma is an atmospheric-pressure plasma of argon or helium.

18. A product selected from an antireflective optical member, a display device, a glass, an eyeglass lens or optical lens, sanitary ware, a microstructure, or stoneware, said product having incorporated therein a surface modifier comprising an organosilicone compound represented by General Formula (A) and/or General Formula (B):

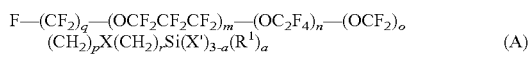
(A)

wherein q is an integer from 1 to 3; m, n, and o are independently integers from 0 to 200, provided that the sum of m, n, and o is 5 or greater; p is 1 or 2; X is O; r is 3; $R^1$ is a $C_{1-22}$ linear or branched hydrocarbon group; a is an integer from 0 to 2; and X' is hydrolysable group; and

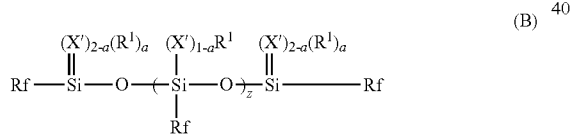
(B)

wherein Rf is F—$(CF_2)_q$—$(OC_3F_6)_m$—$(OC_2F_4)_n$—$(OCF_2)_o(CH_2)_pX(CH_2)_r$—, wherein q is an integer from 1 to 3; m, n, and o are independently integers from 0 to 200, provided that the sum of m, n, and o is 5 or greater; p is 1 or 2; X is O; r is 3; $R^1$ is a $C_{1-22}$ linear or branched hydrocarbon group; a is an integer from 0 to 2; X' is hydrolysable group; and z is an integer from 0 to 10 when a is 0 or 1.

19. The surface modifier according to claim 1 wherein the hydrolysable group is an alkoxy or alkoxy substituted alkoxy group, an acyloxy group, an alkenyloxy group, an iminoxy group, a substituted amino group, an amido group, a substituted aminoxy group, or halogen.

20. A method for producing an organosilicone compound represented by General Formula (B):

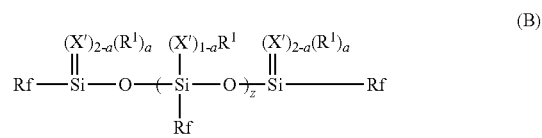
(B)

wherein Rf is F—$(CF_2)_q$—$(OC_3F_6)_m$—$(OC_2F_4)_n$—$(OCF_2)_o(CH_2)_pX(CH_2)_r$—, wherein q is an integer from 1 to 3; m, n, and o are independently integers from 0 to 200, provided that the sum of m, n, and o is 5 or greater; p is 1 or 2; X is O; r is 3; $R^1$ is a $C_{1-22}$ linear or branched hydrocarbon group; a is an integer from 0 to 2; X' is hydrolysable group; and z is an integer from 0 to 10 when a is 0 or 1; the method comprising partially hydrolyzing and then condensing a compound represented by General Formula (A) that is obtained according to the method recited in claim 6.

21. A method for producing an organosilicone compound represented by General Formula (B):

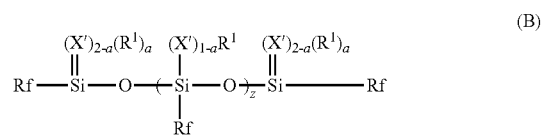
(B)

wherein Rf is F—$(CF_2)_q$—$(OC_3F_6)_m$—$(OC_2F_4)_n$—$(OCF_2)_o(CH_2)_pX(CH_2)_r$—, wherein q is an integer from 1 to 3; m, n, and o are independently integers from 0 to 200, provided that the sum of m, n, and o is 5 or greater; p is 1 or 2; X is O; r is 3; $R^1$ is a $C_{1-22}$ linear or branched hydrocarbon group; a is an integer from 0 to 2; X' is hydrolysable group; and z is an integer from 0 to 10 when a is 0 or 1; the method comprising partially hydrolyzing and then condensing a compound represented by General Formula (A) that is obtained according to the method recited in claim 7.

* * * * *